US009192491B1

(12) United States Patent
Raju et al.

(10) Patent No.: US 9,192,491 B1
(45) Date of Patent: *Nov. 24, 2015

(54) VENOUS STENT

(71) Applicant: Seshadri Raju, Jackson, MS (US)

(72) Inventors: Seshadri Raju, Jackson, MS (US); Peter Neglen, Brandon, MS (US)

(73) Assignee: Seshadri Raju, Jackson, MS (US)

(*) Notice: Subject to any disclaimer, the term of this patent is extended or adjusted under 35 U.S.C. 154(b) by 0 days.

This patent is subject to a terminal disclaimer.

(21) Appl. No.: 14/151,436

(22) Filed: Jan. 9, 2014

Related U.S. Application Data

(63) Continuation of application No. 13/198,917, filed on Aug. 5, 2011, now Pat. No. 8,636,791, which is a continuation of application No. 12/903,056, filed on Oct. 12, 2010, now abandoned, which is a continuation of application No. 12/603,970, filed on Oct. 22, 2009, now abandoned, which is a continuation-in-part of application No. 11/944,094, filed on Nov. 21, 2007, now abandoned.

(60) Provisional application No. 60/866,742, filed on Nov. 21, 2006.

(51) Int. Cl.
A61F 2/06 (2013.01)
A61F 2/852 (2013.01)

(52) U.S. Cl.
CPC .................................... A61F 2/852 (2013.01)

(58) Field of Classification Search
CPC ......... A61F 2/2412; A61F 2/24; A61F 2/852; A61F 2/82
See application file for complete search history.

(56) References Cited

U.S. PATENT DOCUMENTS

| 6,193,745 B1 | 2/2001 | Fogarty et al. |
| 7,520,890 B2 | 4/2009 | Phillips |
| 2001/0044650 A1 | 11/2001 | Simso et al. |
| 2003/0040771 A1 | 2/2003 | Hyodoh et al. |
| 2003/0130726 A1 | 7/2003 | Thorpe et al. |
| 2004/0158312 A1 | 8/2004 | Chouinard et al. |
| 2005/0107863 A1 | 5/2005 | Brown |
| 2005/0131516 A1 | 6/2005 | Greenhalgh |
| 2005/0143806 A1 | 6/2005 | Phillips |
| 2007/0185563 A1 | 8/2007 | Zarbatany et al. |
| 2007/0219618 A1 | 9/2007 | Cully et al. |
| 2009/0118810 A1 | 5/2009 | Klein et al. |
| 2009/0210049 A1 | 8/2009 | Thielen et al. |

OTHER PUBLICATIONS

Neglen, P., M. A. Berry, and S. Raju. "Endovascular Surgery in the Treatment of Chronic Primary and Post-thrombotic Iliac Vein Obstruction." European Journal of Vascular and Endovascular Surgery 20.6 (2000): 560-571.

Raju, Seshadri, Kathryn Hollis, and Peter Neglen. "Obstructive lesions of the inferior vena cava: Clinical features and endovenous treatment." Journal of vascular surgery 44.4 (2006): 820-827.

(Continued)

Primary Examiner — Jason-Dennis Stewart
(74) Attorney, Agent, or Firm — Jones Walker LLP

(57) ABSTRACT

This invention is a modular intraluminal tubular stent system for deployment in the venous system and a method of stenting a vein segment using a modular stent system. One of the stents in the system includes a reinforced terminal end portion, such as a helical coil, to provide additional expansive force to maintain the initial deployed location of the stent. The coil may be interwoven into the wall of the stent, or a separate structure deployed separately.

10 Claims, 5 Drawing Sheets

(56) References Cited

OTHER PUBLICATIONS

Raju, Seshadri, Susan McAllister, and Peter Neglen. "Recanalization of totally occluded iliac and adjacent venous segments." Journal of vascular surgery 36.5 (2002): 903-911.

Neglén, Peter, et al. "Stenting of the venous outflow in chronic venous disease: long-term stent-related outcome, clinical, and hemodynamic result." Journal of vascular surgery 46.5 (2007): 979-990.

Raju, Seshadri, Paul Tackett, and Peter Neglen. "Reinterventions for nonocclusive iliofemoral venous stent malfunctions." Journal of Vascular Surgery (2008).

VENOUS STENT

PRIORITY STATEMENT

This application is a continuation of U.S. application Ser. No. 13/198,917 filed Aug. 5, 2011, which was a continuation of U.S. application Ser. No. 12/903,056 filed Oct. 12, 2010, which was a continuation of U.S. application Ser. No. 12/603,970 filed Oct. 22, 2009, which was a continuation in part of U.S. application Ser. No. 11/944,094 filed Nov. 21, 2007, which claimed the priority benefit of U.S. provisional application No. 60/866,742 filed Nov. 21, 2006. Applicant hereby claims priority to all these applications, and the contents of which are hereby incorporated by reference in their entirety.

BACKGROUND OF THE INVENTION

1. Field of the Invention

The present invention relates generally to endoluminal tubular stents, such as stents and other structures. More particularly, the present invention provides modular tubular stent structures having properties which can be tailored for individual body lumens, including blood vessels, and more particularly, for placement in the venous system.

Stents and related endoluminal devices are currently used by medical practitioners to treat portions of the aorta and peripheral arterial vascular system that have become weakened, developing an aneurysm (a weakening of the artery wall resulting in a distended arterial section that is subject to rupture), or that have become, or portions of the venous vascular system that have become so narrowed that blood flow is restricted (commonly referred to as "stenosis").

Stents are generally cylindrically shaped devices which function to expand when deployed. Stents may be balloon expandable or self expanding. The balloon expandable stent is a stent that is usually made of a coil, mesh or zigzag design. The stent is pre-mounted on a balloon and the inflation of the balloon plastically expands the stent with respect to the balloon diameter. Self-expanding stents are a tubular device stored in an elongate configuration in what is called a delivery system or applicator. The applicator is introduced percutaneously into the body into a vessel at a suitable location, and guided through the vessel lumen to the location where the stent is to be released. The delivery system and the stent are often provided with radiological markers with which the positioning and the release of the stent can be monitored in situ under fluoroscopy. Upon release, the stent material auto expands to a predetermined size.

Commonly used self-expanding stents are braided stents, or laser cut stents. A braided stent is a metal stent that is produced by what is called a plain weaving technique. It is composed of a hollow body, which can stretch in the longitudinal direction and whose jacket is a braid made up of a multiplicity of filament-like elements which, in the expanded state of the braided stent, intersect a plane, perpendicular to the longitudinal direction, at a braid angle. A braided stent undergoes a considerable change in length when deployed ("foreshortening"), this change in length being all the greater the greater the original diameter and the smaller the original braid angle (e.g. Wallstent from Boston Scientific (Boston, Mass. USA)). Because of the considerable shortening that takes place upon release of a braided stent, precise placement is difficult. Laser cut stents are constructed from a tube of material (most frequently, nitinol (a nickel titanium alloy), and also stainless steel, cobalt, etc) that is laser-cut during production to create a meshed device. The tube is comprised of sequential aligned annular rings that are interconnected in a helical fashion. The tube is compressed and loaded into the delivery device and expands to original size when released. Nitinol, which has thermal memory, may help stents made of this material expand into position when exposed to body temperature after delivery. Compared with self-expanding braided stents, laser cut stents provide more accurate stent deployment with less foreshortening. Laser cut stents are much less subject to foreshortening and are probably less rigid than braided stents.

For treatment of aneurysms, the stent generally includes a graft or liner, or may be a liner alone with a stent-like device at each end of the stent for sealing against healthy aortic vessel walls away from the weaken aortic section. The graft or liner is generally made of inelastic non-expanding material, and is generally impermeable to blood, as the stent-graft is intended to prevent blood flow through the liner and into the surrounding artery. Graft material is generally a non-self supporting fabric material that must be attached to the stent frame for support. The combination of a liner and a stent limits the possible radial expansion of the stent, as the liner material is generally inelastic. Constrained expansion of a stent by the liner is desired in the aortic system, as it is not desired to have the liner-stent seal against unhealthy distended aortic tissue—rather, the liner stent is deployed to create a sealed passage through the weakened aortic section and to prevent blood flow between the exterior surface of the liner/stent combination (or liner alone) and the weaken aortic walls, thereby preventing the possible rupture or bursting of the weakened aortic walls.

In the venous system, the setting is different—the issue is not weakened vessel walls, but stenosis within the vessel. Venous stenosis may be caused by clotting, scarring following blood clots or by focal external compressive forces on a venous vessel (such as in the femoral vein where it crosses the inguinal ligament or in the pelvic vein where it is crossed by overlaying pelvic arteries). In treating a venous stenosis, a liner or graft is not necessary; indeed, a liner or graft is not preferred, as the stent must function to expand against the narrowed vein section, thereby expanding the narrowed section to a more normal cross-sectional area. It is not desired to limit expansion a stent used for treating stenosis in the venous system.

While stents in the venous system are most often used to "prop open" blood vessels, they can also be used to reinforce collapsed or narrowed tubular structures in the body, such as the respiratory system, the reproductive system, or any other tubular body structure. These stents are generally mesh-like so that endothelial and other cells can grow through the openings integrating the stent into the venous wall and sometimes resulting in restenosis of the tubular structure. Inclusion of liners or grafts would prevent the integration of the stent into the venous wall. Typically, one or both ends of the stent is flared in order to facilitate anchoring within the vessel.

Most stents are designed to work in fairly small lumens and are relatively short in length. However, lumens in the venous system can be much larger than aorta and peripheral arteries and the desired stent length can be long in comparison to arterial stents. Both features of the venous system present problems for conventional stent design, where the conventional stent structure is typically formed with cylindrical frames having axially constant diameters and constant expansive forces along their lengths. Additionally, long length stent structures may also encounter variations in lumen size over the venous application length, making placement and use of a single sized cross-sectional sized stent problematic. One method to accommodate the different lumen diameters in the aortic system is with a modular stent system as shown in U.S.

Pat. No. 6,193,745, hereby incorporated by reference. However, in this stent system, compressive/expansive forces on one modular section tend to shorten or lengthen the particular section, allowing for relative movement between adjacent modular stent sections, not desired in a venous system application. Such movement is not desirable, particularly where proper stent placement is critical to accommodate intersecting veins. Additionally, this system is designed for aneurysms, and hence, liners are employed.

In order to overcome some or all of these drawbacks, a stent system is needed that can account for the difficulties of placement within the venous system and to accommodate variations in geometry along body lumens without compromising the effectiveness of the stent. It would further be desirable to provide adaptable modular stents and methods for their placement which would facilitate effective treatment of widely varying luminal system geometries without requiring the maintenance of a large inventory of stent module models.

2. Summary of the Invention

The present invention provides modular intraluminal tubular stents for deployment in the venous system. The stents can be utilized in a modular system, allowing placement of multiple overlapping stents to form a composite stent structure having characteristics which are tailored to the specific requirements of the patient. A particular modular stent may have an opening or fenestra in the sidewall to accommodate flow from a side vein that joins the vein where the modular stent is positioned. A modular stent may have reinforced portions where the stent side wall material is varied for particular reasons, for instance, to add reinforcement to a portion of the stent that is subject to greater focal compressive/expansive radial body forces (a compressive force is one applied that tends to bend the stent or collapse the stent inwardly). Additionally, a stent may have a reinforced terminal end to provide additional expansive force to maintain the initial deployed location of the stent. The reinforced section extends from near one end of the stent to suitable distance back from that end, for instance form several mm to 40 mm, but generally not more than ¼ or at most, ½ the length of the stent. Modification of the construction of stent sidewall materials (such as by the addition of additional reinforcing expansive rings or variable geometry) can be made in desired portions of the stent to provide a "customized" modular stent section that can have varying axial (lengthwise) properties, or a helical expansive ring may be joined with the stent (e.g. attached to the stents interior or exterior sidewall, or interwoven into the side wall). A separate reinforcement stent (a small stent having either greater expansion characteristics or greater resistance to compressive forces) or a separate helical coil may also be used in conjunction with a venous stent or venous stent module. Stent modules may be combined to form longer stent structures as needed to fit the needs of individual patients.

DESCRIPTION OF THE SPECIFIC EMBODIMENTS

Construction details for stents are well known in the art. The stent modules will generally be radially expandable from a narrow-diameter configuration to facilitate introduction into the body lumen via catheter, and are constructed without a liner or graft. The tubular or cylindrical structure generally comprises a series of independent rings that are interwoven or interlaced to create an elongated tubular structure. Alternatively, the stent can be constructed as a braided tubular structure, much like a Chinese finger. By varying the braid pattern or density of the braids (or braid material) or the rings, or the braid or ring material, a particular stent module can be customized as desired for varying the expansive force, or for varying the resistance to compressive forces, along the length of the stent.

Figure 1:
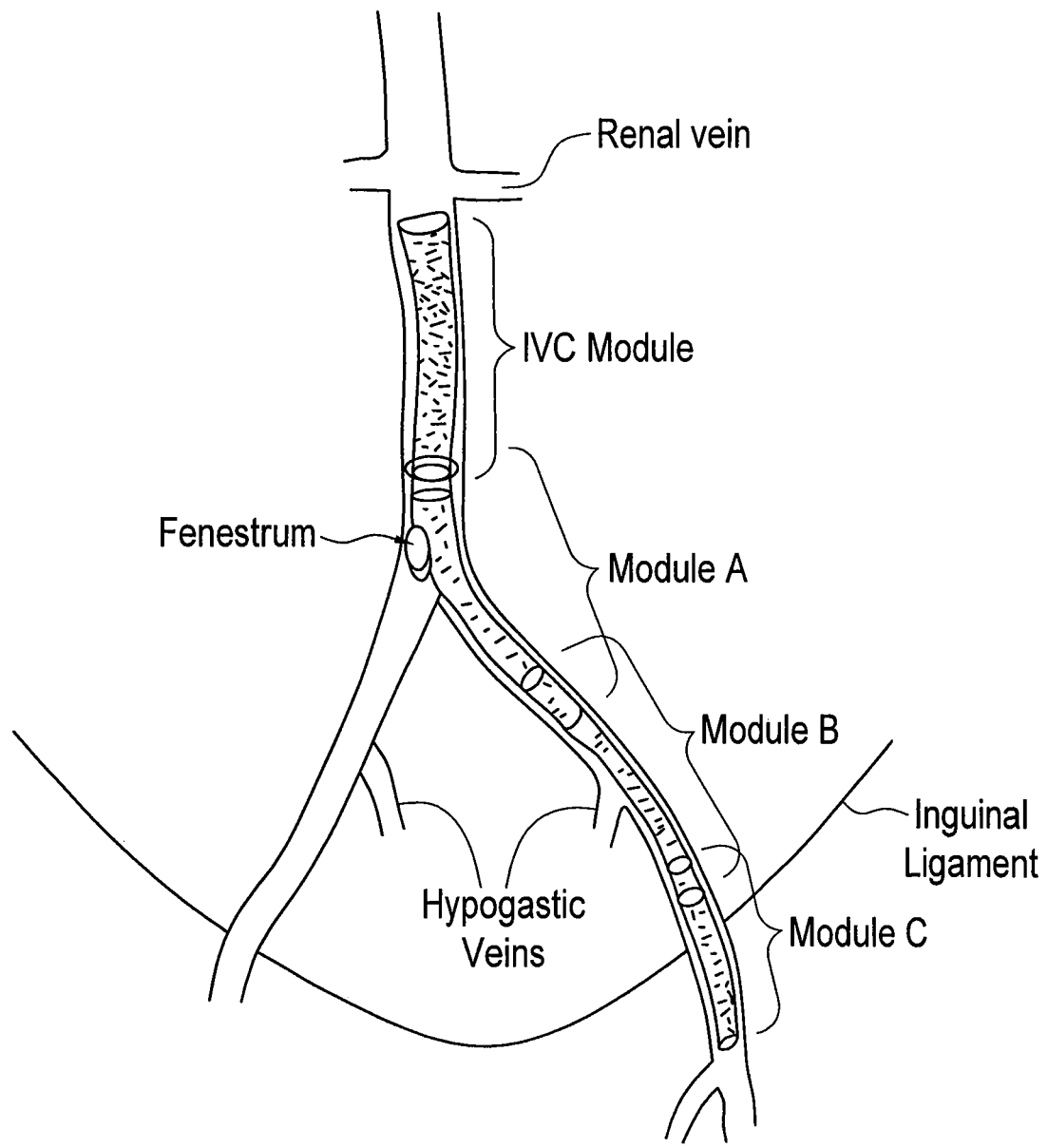
FIG. 1 is a depiction showing a four stent module application (module A, B, C, and IVC Module) deployed in the pelvic venous system.
Figure 2A:
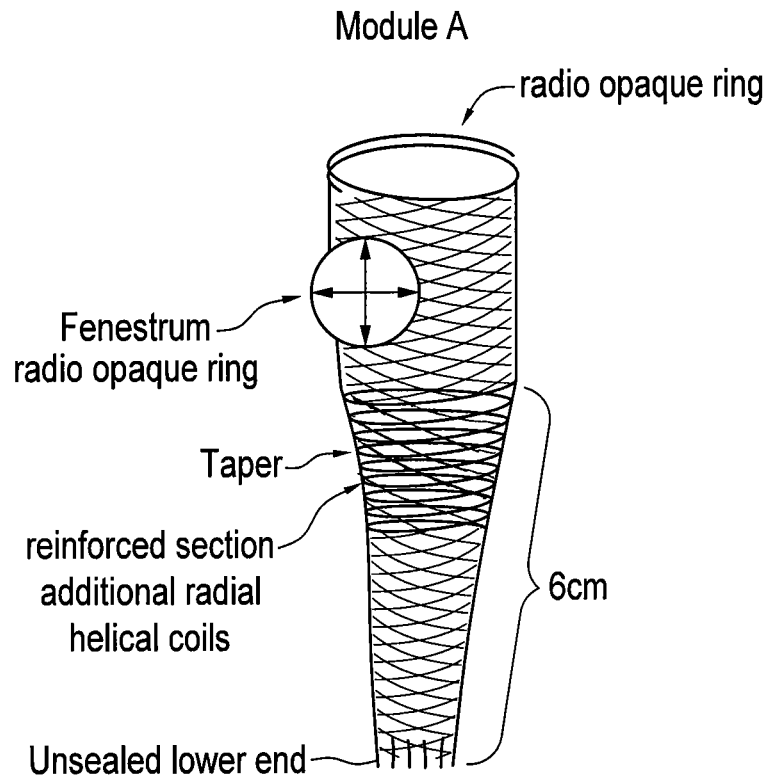
FIG. 2A is a depiction of module A depicted in FIG. 1, showing a side aperture and tapered body, and non-reinforced lower end.
Figure 2B:
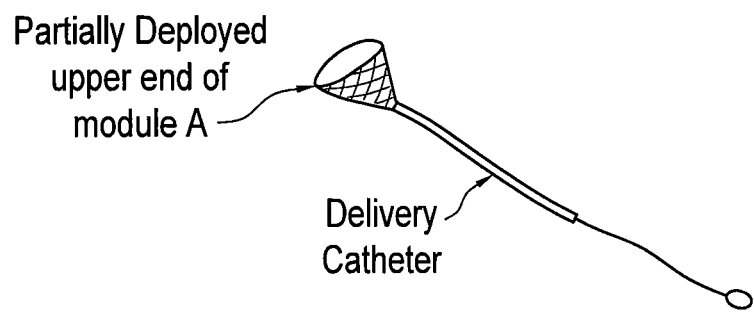
FIG. 2B is a depiction showing module A being deployed from the distal end of a catheter.
Figure 3A:
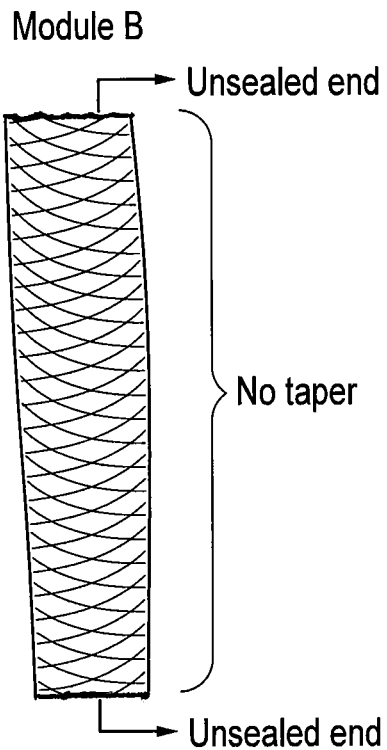
FIG. 3A is a depiction showing module B with both ends non-reinforced or unsealed.
Figure 3B:
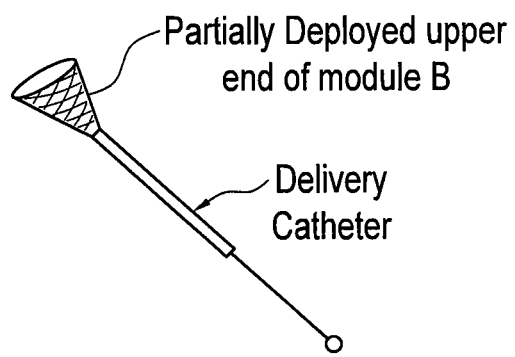
FIG. 3B is a depiction showing module B being deployed from the distal end of a catheter.

The operational requirements of a specific venous stent structure must account for the environmental placement. Venous stents are most likely to be employed in the pelvic veins, and commonly extend from the inferior vena cava (typical size about 21 to 25 mm average) to a landing site below. The caudal landing site may be in the common iliac vein (14-16 mm size average), external iliac vein (12-14 mm size average) or the common femoral vein below the inguinal ligament. To accommodate differing caudal landing sites, and therefore the different lengths, the design should be modular to account for differing lumen diameters. One particular embodiment is shown in FIG. 1. Shown is a four stent module application. The stent structure starts at the inferior vena cava (IVC) which is the largest of the veins for this particular application, and ends in a much smaller vein below. The first stent module extends from the vena cava to the common iliac vein (module A), the second stent module extends from the common iliac vein to the external vein band (module B) the third stent module extends from the external iliac vein to the common femoral vein (module C) (these stent modules can be used alone or in combination as needed). Typical stent diameters and lengths for the venous system are indicated in the drawings.

When two or more stent modules are employed together to create a long stent structure, an overlap is desired between the adjacent stents (generally an overlap 3 to 4 cm can be utilized). Hence, the length of each module does not have to be exact and conform to the anatomical conditions, but can be somewhat shorter or somewhat longer, even stents with deployed diameters larger than then native vein segment may be used. The differences in adjacent overlapped stent segments will be accounted for in the overlapped region. The uppermost module, if starting in the vena cava, needs to accommodate flow that enters from the opposite iliac vein. An aperture, opening or fenestra is thus constructed into the sidewall of the tubular stent body for this purpose. As bilateral stents are sometimes necessary, the fenestra can also be employed for placement of an intersecting or joining stent.

There are several pressure points along the course of these veins, and enforcement of the stents at these points are desirable. Reinforcement can be accomplished by placing a reinforcing liner stent (a separate stent, constructed without a liner or graft, and used to line a portion of a modular stent section) on the interior of a pre-positioned deployed stent module or a reinforcing coil stent, such as a helical coiled spring. Alternatively, the coil structure may be integrated into the stent wall, or, a reinforcing stent module (e.g., a reinforcement stent) can be first positioned in the vein and a second stent module positioned through and interior to the reinforcement stent (and generally extending beyond) the reinforcement stent. Finally, the stent module may have a reinforcing section constructed within or interwoven with, the tubular structure, such as by varying the construction materials of the stent in the portion to be reinforced (e.g., adding additional and closer spaced rings to the stent tubular body, varying the construction materials (stiffer materials), etc.). Stent body module construction may further vary a number of stent characteristics, including length, cross-section, flexibility, resilient spring force, and conformability.

Figure 6A:
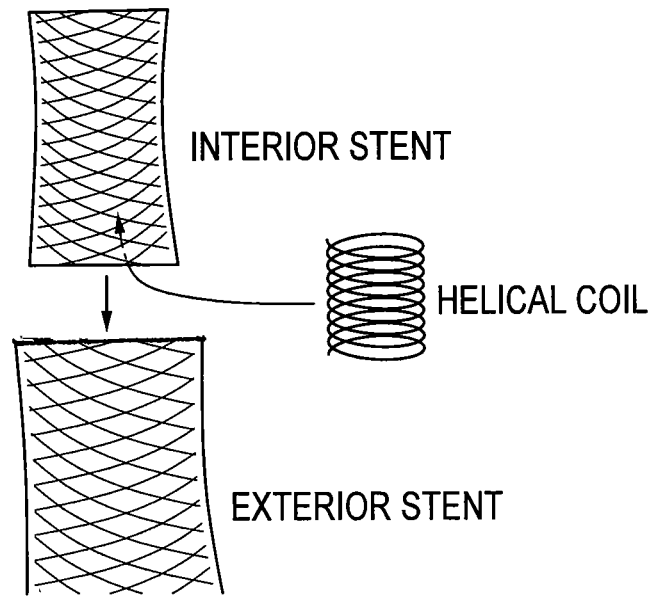
FIG. 6A is a schematic showing the relationship of an interior stent, exterior stent and reinforcing coil.
Figure 6B:
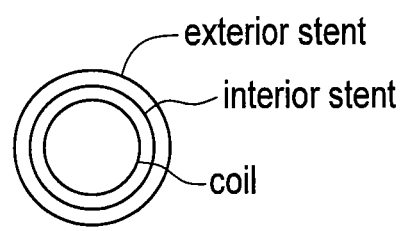
FIG. 6B is a cross section through the assembled stents of FIG. 6A, showing the geometry of the completed stent system.

When the stent is compressed by pressure points in the veins, the stent body will tend to shorten or lengthen, and the stent may contract at the upper and lower ends of the stent. With stents constructed of interwoven spiral metal wires, such movement is more likely. This movement is undesirable as placement of the stent ends can alter the critical placement of the stent components (such as the movement of a side fenestra's placement). In a modular stent system, this movement can alter the degree of overlap of adjacent stents, and if overlap is not sufficient, could result in an unstented section within the extended stent system, an undesired condition, as such unstented sections are more prevalent to developing recurrent blockage. In overlapped stent modules, one module is exterior (exterior surface in the overlapped region facing the vessel sidewalls), while the other stent module is the interior stent (exterior surface in then overlapped region faces the interior surface of the exterior stent. To prevent movement of adjacent stents, overlapped sections can be coupled or anchored to adjacent stents (see FIGS. 6A and 6B), or in the alternative, have sufficient overlap (in a non-fenestra section) to accommodate possible contractions or expansions. Individual stent sections may have anchors that will prevent movement of that anchor point within the lumen walls, by anchoring to the lumen walls. For instance, in a three stent system deployed in the pelvic veins (see FIG. 1), maintaining the upper stent module's placement (module A) and lower stent module's placement (module C) are more critical. Anchoring both ends of the extended stent structure firmly in the vein wall will prevent migration of the structure two ends of the structure. As shown, in module A, the terminal end (which may not be interior to another stent, if the IVC module is not needed) as shown, has a sealing ring or anchor (an expandable helical ring) near the end of the stent containing the fenestrum, thereby maintaining the proper orientation and placement of the fenestrum. The middle module, module B, is not necessarily anchored, provided sufficient overlap is present to accommodate movement between adjacent stent modules. Lacking such overlap, an anchor or sealing ring is desired in the overlap region, with the sealing ring positioned on the interior stent, either integrated into the stent sidewalls, or a separate anchor ring positioned on the interior surface of the interior stent. The sealing ring is designed to be more expansive than the remainder non-reinforced portions of the stent body; the sealing ring firmly anchors the interior stent end to the exterior stent, and the exterior stent to the vein wall (see FIGS. 6A and 6B). The third stent (module C) has a reinforcing ring positioned at the lower end, anchoring the lower terminus of the extended sting structure to the lumen walls.

As described, each stent module is radially expandable and has a generally tubular body portion and first and second terminal end portions, with no liner or graft. In adjacent overlapped sections, when anchoring is done, it is preferred that the interior stent module have more spring force in a portion of the overlapped region to help ensure that the stent modules are engaged with one another and resist relative motion between the modules in the overlapped region.

The desired coupling or anchoring can be accomplished by having the anchoring stent end reinforced with slightly more expansive spring force, thereby mechanically assisting the coupling between the stent module and an adjacent stent or the lumen walls. This coupling can be accomplished also by placement of a helical spring or sealing collar in the interior of the interior stent module (which may be placed at the same time or after placement of the stent). Hooks in the exterior surface of the interior stent walls have been used to couple stent segments together—this arrangement is not preferred, as hooks can also engage vessel side walls, causing damage if the stent moves. When a sealing collar, such as a helical coil, is used, the coil will be small compared to the stent module—for instance, the coil may be a section 2 cm long, while the surrounding stent module may be 10 cm in length. Alternatively, the helical coil may be interwoven or integrated into the body of the stent, for instance, by weaving a helical coil spring through the terminal rings of the stent, or welding the helical coil to the stent rings or terminal stent ring, or other such manufacturing technique (placement of a terminal expansive ring member on the stent is considered as sealing that end of the stent). Such additional expansive forces on the terminal end of the stent body (or even on the interior of the stent body) will help lock the reinforced region with the contacting surface. When only one end of the stent is "sealed" or reinforced, the stent ends will move (lengthen or contract) primarily only at the unsealed or non-reinforced end, when the stent body is subject to compressive or tensile forces.

Figure 4A:
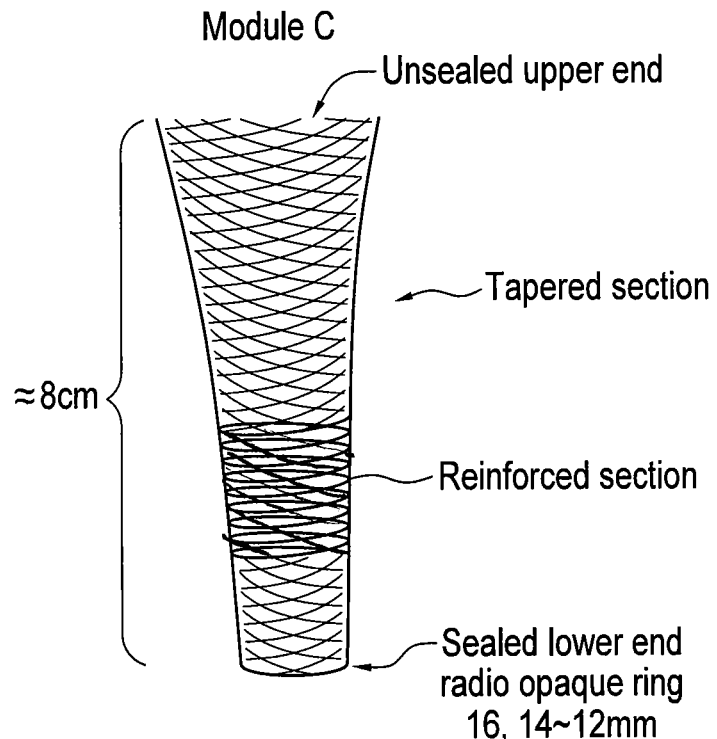
FIG. 4A is a depiction showing stent module C having tapered body, and reinforce section, sealed lower end and unsealed upper end.
Figure 4B:
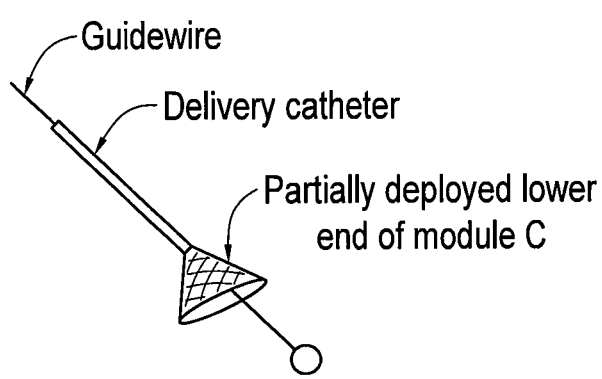
FIG. 4B is a depiction showing deployment of module C from the proximal end of a catheter.
Figure 5:
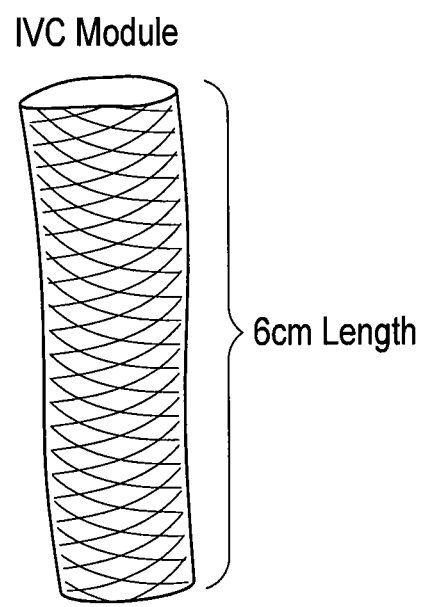
FIG. 5 is a depiction of the IVC stent module.

Generally, the beginning and landing sites have to be precise, therefore, the uppermost module should be deployed from the top (distal) of the catheter housing the stent, while the lowest module should be deployed from the bottom (proximal) of the stent housing (like opening an umbrella, see FIG. 4B). Such deployment ensures accuracy in placement of the stent modules. It may be also be desirable to include helical expansive rings near a side fenestrum (such as near one side of the opening, or near both sides of the opening), to resist movement of the stent in the area of the fenestrum, as movement can cause misalignment of the fenestrum with the opening in the vessel.

As described, modular sections of the stent structure, or stent modules, may be selectively combined to form a composite stent having characteristics which are tailored to the specific requirements of the patient. Each stent module can include reinforced sealing ends (one or both) for coupling to adjacent modules with additional spring force. Alternatively, a particular stent module may have discrete "reinforced" sections (for instance, a section that is up to ½ the length of the overall stent) either built into the stent module itself or provided by deployment of an additional "reinforcing stent module" by catheter into the interior of a previously deployed stent module. The supplemental "reinforcement stent," a second stent generally smaller in length (without a liner or graft) that has the needed characteristics, may be deployed internal to a stent module, or if reinforcement against compressive forces is desired, may be deployed first, and the stent module deployed through the reinforcement stent.

The stent modules can vary in axial length, cross-section, perimeter, resilient expansive force (spring force), flexibility, or other desired characteristics, and also along the axis of each stent module. Selection of appropriate stent modules and of the degree of overlap provides a custom fit stent. If a reinforced segment is desired, a separate short stent, suitable to cover the area requiring reinforcement, may be added. The reinforce segment may have the same rigidity characteristics as the exterior stent, as in the region of the double stent, the effective device wall thickness will be greater than that of the exterior stent, thus providing the desired additional resistance to compression. A stent module can be constructed to have a varying diameter along its length (e.g., a taper), to accommodate variation in the venous lumen diameter. This can be accomplished by varying the construction of the stent module along its length, such as by having the body of the stent constructed of varying diameter intermeshing or interlocking ring segments.

The modules are preferably individually introduced into a lumen system of a patient's body one at a time so that the composite stent is assembled in situ. It is preferred that the ends of the stent modules contain dense radio opaque material to assist in placement of the modules through fluoroscopy techniques. For instance, integrated helical rings may be formed of radio opaque materials.

The invention claimed is:

1. A stent system comprising a first and second expandable stent, each of said stents comprising a wall surface when expanded having a hollow interior forming an interior surface and an exterior surface, each of said stents having a first terminal end and a second terminal end and a length defined by the distance between said first and second terminal ends, each of said stents, along the length of each of said of stents, when expanded, are sized to be greater in diameter than the tubular lumen into which each of said stents is intended to be deployed, the first terminal end of said first stent (the "interior stent") configured to be placed interior the second terminal end of the second stent (the "exterior stent") and to resist sliding of the first terminal end of said interior stent with respect to said second terminal end of said exterior stent when said interior stent is deployed interior to said exterior stent, where the configuration to resist sliding comprises a reinforced section, said reinforced section comprising an expandable helical coil not constrained by a liner, said reinforced section providing expansive spring force greater than that provided by the second terminal end of said exterior stent.

2. The stent system of claim 1 wherein said expansive helical coil is formed in or attached to the wall surface of said interior stent's first terminal end.

3. The stent system of claim 1 wherein said expansive helical coil is separate from said wall surface of said interior stent.

4. The stent system of claim 1 wherein one of said first or second stents has an opening in said wall surface sized, when expanded, to accommodate a branch vein opening in a venous segment.

5. The stent system of claim 4, wherein said wall surface of said stent containing said opening further comprises a second reinforced section adjacent said opening.

6. The stent system of claim 1 wherein one of said first or second stents has a tapered section.

7. A stent system comprising a first and second expandable stent, each stent configured to expand in a vein comprising a tubular tissue wall, each stent when expanded, having a wall surface forming an interior surface and an exterior surface, each of said stents having a first terminal end and a second terminal end and a length defined by the distance between said first and second terminal ends, each of said first and second stents, when expanded and positioned at a location in a vein, sized to have the respective exterior surface, substantially along the length of the respective stent, be in contact with either the vein tissue wall or the other stent, whereby said first stent, at said first stent's first terminal end, overlaps said second stent at said second stent's second terminal end, said first stent's first terminal end being interior said second stent's second terminal end, said first stent's first terminal end further comprising a reinforced section, said reinforced section not constrained by a liner and providing more expansive spring force than the second terminal end of said second stent.

8. The stent system of claim 7 wherein said reinforced section comprises an expandable helical coil or ring.

9. The stent system of claim 8 wherein said helical coil or ring is interwoven into the first stent's first terminal end.

10. The stent system of claim 8 wherein said helical coil or ring is a separate ring or coil.

* * * * *